United States Patent
Lange et al.

(10) Patent No.: US 10,470,692 B2
(45) Date of Patent: Nov. 12, 2019

(54) SYSTEM FOR PERFORMING PULSE OXIMETRY

(71) Applicant: ChroniSense Medical Ltd., Yokneam (IL)

(72) Inventors: Daniel H. Lange, Kfar Vradim (IL); Boris Karelin, Haifa (IL)

(73) Assignee: ChroniSense Medical Ltd., Yokneam (IL)

( * ) Notice: Subject to any disclaimer, the term of this patent is extended or adjusted under 35 U.S.C. 154(b) by 492 days.

(21) Appl. No.: 14/738,711

(22) Filed: Jun. 12, 2015

(65) Prior Publication Data

US 2016/0361003 A1 Dec. 15, 2016

(51) Int. Cl.
*A61B 5/1455* (2006.01)
*A61B 5/00* (2006.01)

(52) U.S. Cl.
CPC ...... *A61B 5/14551* (2013.01); *A61B 5/14552* (2013.01); *A61B 5/681* (2013.01); *A61B 5/7203* (2013.01); *A61B 5/7214* (2013.01); *A61B 5/6816* (2013.01); *A61B 5/6823* (2013.01); *A61B 5/6824* (2013.01); *A61B 5/6826* (2013.01); *A61B 5/6829* (2013.01); *A61B 2560/0223* (2013.01); *A61B 2562/0233* (2013.01)

(58) Field of Classification Search
None
See application file for complete search history.

(56) References Cited

U.S. PATENT DOCUMENTS

| | | | |
|---|---|---|---|
| 3,885,552 | A | 5/1975 | Kennedy |
| 3,898,984 | A | 8/1975 | Mandel et al. |

(Continued)

FOREIGN PATENT DOCUMENTS

| | | |
|---|---|---|
| EP | 2430975 A1 | 3/2012 |
| EP | 3307146 | 4/2018 |

(Continued)

OTHER PUBLICATIONS

"International Search Report" and "Written Opinion of the International Searching Authority," Patent Cooperation Treaty Application No. PCT/IL2017/050242, dated Jun. 13, 2017, 12 pages.

(Continued)

*Primary Examiner* — Etsub D Berhanu
(74) *Attorney, Agent, or Firm* — Carr & Ferrell LLP

(57) ABSTRACT

Provided are a method and systems for performing pulse oximetry. A light signal is emitted for a period of time and a modulated light signal is detected. The modulated light signal includes a red signal and an infrared signal. The modulated light signal is originated by an interaction of the light signal with a pulsatile tissue and a non-pulsatile tissue. The modulated light signal is processed to estimate an oxygen saturation in the pulsatile tissue during the period of time. The processing includes removing a non-pulsatile component resulting from the interaction of the light signal and the non-pulsatile tissue. The non-pulsatile component can be removed by removing a first parameter from an intensity of the infrared signal and a second parameter from an intensity of the red signal. The parameters are predetermined using a calibration process to reproduce a true value for a ratio used to determine the oxygen saturation.

18 Claims, 11 Drawing Sheets

(56) References Cited

U.S. PATENT DOCUMENTS

| | | | |
|---|---|---|---|
| 4,331,154 A | 5/1982 | Broadwater et al. | |
| 4,732,158 A | 3/1988 | Sadeh | |
| 4,802,486 A | 2/1989 | Goodman et al. | |
| 5,316,008 A | 5/1994 | Suga et al. | |
| 5,503,148 A * | 4/1996 | Pologe | A61B 5/14551 128/925 |
| 5,692,505 A * | 12/1997 | Fouts | A61B 5/1455 356/41 |
| 6,047,203 A | 4/2000 | Sackner et al. | |
| 6,139,494 A | 10/2000 | Cairnes | |
| 6,527,725 B1 | 3/2003 | Inukai et al. | |
| 7,479,111 B2 | 1/2009 | Zhang et al. | |
| 7,544,168 B2 | 6/2009 | Nitzan | |
| 7,738,935 B1 * | 6/2010 | Turcott | A61B 5/0261 600/336 |
| 8,172,764 B2 | 5/2012 | Gregson et al. | |
| 8,602,997 B2 | 12/2013 | Banet et al. | |
| 8,866,606 B1 | 10/2014 | Will et al. | |
| 2001/0005773 A1 * | 6/2001 | Larsen | A61B 5/14551 600/323 |
| 2001/0029326 A1 * | 10/2001 | Diab | A61B 5/14551 600/364 |
| 2002/0095077 A1 * | 7/2002 | Swedlow | A61B 5/14551 600/323 |
| 2002/0133068 A1 | 9/2002 | Huiku | |
| 2003/0009091 A1 * | 1/2003 | Edgar, Jr. | A61B 5/14551 600/323 |
| 2003/0109776 A1 | 6/2003 | Jacques | |
| 2003/0163033 A1 * | 8/2003 | Dekker | A61B 5/0205 600/323 |
| 2004/0215095 A1 * | 10/2004 | Lee | A61B 5/14551 600/529 |
| 2005/0070775 A1 * | 3/2005 | Chin | A61B 5/14552 600/323 |
| 2005/0281439 A1 | 12/2005 | Lange | |
| 2006/0074322 A1 | 4/2006 | Nitzan | |
| 2006/0264767 A1 | 11/2006 | Shennib | |
| 2007/0142720 A1 * | 6/2007 | Ridder | A61B 5/14532 600/336 |
| 2007/0191725 A1 | 8/2007 | Nelson | |
| 2008/0146954 A1 | 6/2008 | Bojovic et al. | |
| 2008/0208069 A1 | 8/2008 | John et al. | |
| 2008/0214961 A1 | 9/2008 | Matsumoto et al. | |
| 2008/0221419 A1 * | 9/2008 | Furman | A61B 5/0031 600/324 |
| 2008/0255433 A1 | 10/2008 | Prough et al. | |
| 2009/0024011 A1 | 1/2009 | Huiku | |
| 2009/0247848 A1 * | 10/2009 | Baker, Jr. | A61B 5/14551 600/323 |
| 2010/0016694 A1 | 1/2010 | Martin et al. | |
| 2010/0217144 A1 | 8/2010 | Brian | |
| 2010/0298656 A1 | 11/2010 | McCombie et al. | |
| 2010/0312079 A1 * | 12/2010 | Larsen | A61B 5/742 600/323 |
| 2010/0324384 A1 * | 12/2010 | Moon | A61B 5/1118 600/323 |
| 2011/0066051 A1 | 3/2011 | Moon et al. | |
| 2011/0077486 A1 | 3/2011 | Watson et al. | |
| 2011/0082355 A1 | 4/2011 | Eisen et al. | |
| 2011/0201946 A1 * | 8/2011 | Turcott | A61B 5/1455 600/484 |
| 2011/0224564 A1 | 9/2011 | Moon et al. | |
| 2012/0190944 A1 | 7/2012 | Thaveeprungsriporn et al. | |
| 2013/0231947 A1 | 9/2013 | Shusterman | |
| 2013/0296665 A1 | 11/2013 | Kassim et al. | |
| 2013/0296666 A1 | 11/2013 | Kumar et al. | |
| 2013/0296673 A1 * | 11/2013 | Thaveeprungsriporn | G01N 21/3151 600/324 |
| 2013/0338460 A1 | 12/2013 | He et al. | |
| 2014/0088449 A1 | 3/2014 | Nearing et al. | |
| 2014/0142445 A1 | 5/2014 | Banet et al. | |
| 2014/0206948 A1 | 7/2014 | Romem | |
| 2014/0275888 A1 | 9/2014 | Wegerich et al. | |
| 2015/0196257 A1 | 7/2015 | Yousefi et al. | |
| 2015/0320328 A1 | 11/2015 | Albert | |
| 2015/0366518 A1 | 12/2015 | Sampson | |
| 2016/0022220 A1 | 1/2016 | Lee et al. | |
| 2016/0089033 A1 | 3/2016 | Saponas et al. | |
| 2016/0270677 A1 | 9/2016 | Lin | |
| 2016/0360971 A1 | 12/2016 | Gross et al. | |
| 2016/0360974 A1 | 12/2016 | Lange | |
| 2016/0360986 A1 | 12/2016 | Lange | |
| 2016/0361004 A1 | 12/2016 | Lange et al. | |
| 2017/0014037 A1 | 1/2017 | Coppola et al. | |
| 2017/0202459 A1 | 7/2017 | Cao | |
| 2017/0258406 A1 | 9/2017 | Lange | |
| 2018/0098705 A1 | 4/2018 | Chaturvedi et al. | |
| 2018/0132794 A1 | 5/2018 | Lange | |

FOREIGN PATENT DOCUMENTS

| | | |
|---|---|---|
| EP | 3307150 | 4/2018 |
| EP | 3307162 | 4/2018 |
| WO | WO2001015597 | 3/2001 |
| WO | WO2014022906 A1 | 2/2014 |
| WO | WO2015197383 A1 | 12/2015 |
| WO | WO2016199121 A1 | 12/2016 |
| WO | WO2016199122 A1 | 12/2016 |
| WO | WO2016199123 A1 | 12/2016 |
| WO | WO2016199124 A1 | 12/2016 |
| WO | WO2015070030 A1 | 1/2017 |
| WO | WO2017158585 A1 | 9/2017 |
| WO | WO2018025257 A1 | 2/2018 |

OTHER PUBLICATIONS

Abtahi, Farhad, "Feasibility of Fetal EEG Recording," Master's Thesis, Department of Signal and System, Chalmers University of Technology, Gothenburg, Sweden, Jan. 1, 2011, 51 pages.

Richardson, Kelly et al., "Electrocardiographic damage scores and cardiovascular mortality," American Heart Journal vol. 149, No. 3, Mar. 1, 2005, pp. 458-463.

Non-Final Office Action, dated Oct. 5, 2016, U.S. Appl. No. 14/738,636, filed Jun. 12, 2015.

Non-Final Office Action, dated Oct. 5, 2016, U.S. Appl. No. 14/738,666, filed Jun. 12, 2015.

Patent Cooperation Treaty Application No. PCT/IL2016/050512, "International Search Report" and "Written Opinion of the International Searching Authority," dated Sep. 18, 2016, 9 pages.

Arza et al., "Pulse Transit Time and Pulse Width as Potential Measure for estimating Beat-to-Beat Systolic and Diastolic Blood Pressure", Computing in Cardiology 2013, pp. 887-890.

Ye et al., "Estimation of Systolic and Diastolic Pressure using the Pulse Transit Time", International Journal of Medical, Health, Biomedical, Bioengineering and Pharmaceutical Engineering vol. 4. No. 7, 2010, pp. 303-308.

International Search Report and Written Opinion dated Jul. 11, 2016 in Patent Cooperation Treaty Application No. PCT/IL2016/050511 filed May 15, 2016, pp. 1-19.

International Search Report and Written Opinion dated Aug. 18, 2016 in Patent Cooperation Treaty Application No. PCT/IL2016/050514 filed May 15, 2016, pp. 1-20.

International Search Report and Written Opinion dated Aug. 29, 2016 in Patent Cooperation Treaty Application No. PCT/IL2016/050513 filed May 15, 2016, pp. 1-18.

"International Search Report" and "Written Opinion of the International Searching Authority," Patent Cooperation Treaty Application No. PCT/IL2017/050826, dated Oct. 23, 2017, 9 pages.

Final Office Action, dated Mar. 22, 2017, U.S. Appl. No. 14/738,636, filed Jun. 12, 2015.

Final Office Action, dated Mar. 29, 2017, U.S. Appl. No. 14/738,666, filed Jun. 12, 2015.

Non-Final Office Action, dated May 17, 2017, U.S. Appl. No. 15/226,881, filed Aug. 2, 2016.

Advisory Action, dated Jun. 16, 2017, U.S. Appl. No. 14/738,636, filed Jun. 12, 2015.

(56) References Cited

OTHER PUBLICATIONS

Non-Final Office Action, dated Aug. 16, 2017, U.S. Appl. No. 15/069,739, filed Mar. 14, 2016.
Non-Final Office Action, dated Sep. 5, 2017, U.S. Appl. No. 14/738,636, filed Jun. 12, 2015.
Non-Final Office Action, dated Sep. 8, 2017, U.S. Appl. No. 14/738,666, filed Jun. 12, 2015.
Final Office Action, dated Sep. 18, 2017, U.S. Appl. No. 15/226,881, filed Aug. 2, 2016.

* cited by examiner

SYSTEM FOR PERFORMING PULSE OXIMETRY

CROSS-REFERENCE TO RELATED APPLICATIONS

The present application is related to U.S. patent application Ser. No. 14/738,666, filed Jun. 12, 2015 and titled "Monitoring Health Status of People Suffering from Chronic Diseases" and U.S. patent application Ser. No. 14/738,636, filed Jun. 12, 2015 and titled "Wearable Device Electrocardiogram". The disclosures of the aforementioned applications are incorporated herein by reference for all purposes.

FIELD

The present application relates to systems and methods for monitoring health status of people, and more specifically to systems and methods for performing pulse oximetry.

BACKGROUND

It should not be assumed that any of the approaches described in this section qualify as prior art merely by virtue of their inclusion in this section.

Pulse oximetry is a method for estimating blood oxygen saturation by utilizing specialized light sources and optical sensors. Tuned light wavelengths are either transmitted through or reflected from a human tissue and are used to estimate a relative proportion of oxygenated blood. This estimated oxygen saturation, termed $SpO_2$, is generally strongly related to arterial blood oxygen saturation. The main advantages of the pulse oximetry over other methods of determining oxygen saturation, such as blood sampling, is that the pulse oximetry is non-invasive, minimally intrusive, generally not painful, portable if it needs to be, and provides for continuous readings.

For a healthy human being at normal altitudes, $SpO_2$ is typically 95% or above, 90% or below indicating hypoxemia, and sustained periods of 80% or below possibly resulting/indicating serious medical complications. $SpO_2$ can reflect statuses of individuals suffering from various clinical disorders such as the Chronic Obstructive Pulmonary Disease (COPD) or asthma, whether in a stable chronic condition or during an acute phase. Pulse oximetry is also useful in neonatal monitoring, surgical monitoring, or status evaluation when the possibility of oxygen depletion must be considered (pilot monitoring, deep sea diving, and so forth).

Certain clinical conditions can interfere with either the accuracy of pulse oximetry or affect interpretation of results. Diseases which affect peripheral circulation can make the $SpO_2$ an inaccurate estimate of arterial oxygenation; anemia will impede utilization of blood oxygen, whatever the saturation level.

Human activity and behavior can also affect results of the pulse oximetry measurements. Movement of the sensor used in pulse oximetry can interfere with signal acquisition. Temperature changes can affect blood flow to the area being monitored with the sensor. Sweating can affect optical quality. Smoking can increase carbon monoxide which competes with oxygen to bind hemoglobin and can confuse most systems. Contrast dye injections can interfere with blood optical qualities.

Pulse oximetry depends on differences in light absorbance characteristics of oxygenated hemoglobin (oxyhemoglobin) and non-oxygenated hemoglobin (deoxyhemoglobin). The former absorbs light at about 660 nm (in the visible red range) and the latter absorbs light at about 940 nm (infrared). Both light signals, whether reflected or transmitted, fluctuate with the arterial pulse. The resulting signals, photoplethysmograms (PPGs) can indicate volume changes due to blood flow. Pulse oximetry utilizes the intensity change (light signal fluctuation at each heartbeat) for each wavelength to eliminate the confounding optical effects of other tissues (which remain constant). $SpO_2$ can be estimated using the Beer-Lambert Law, which relates to light absorbance due to the concentration of a substance in media, and empirically-derived reference curves from blood samples of hypoxic volunteers, based on the ratio of these changes in each wavelength (delta 660 nm/delta 940 nm), although other complex factors are often included in the calculations.

Typically, the light sources are light-emitting diodes (LEDs) optimized for output at each of the target wavelengths. A single optical sensor (often a photodiode) may be used for both. Each LED can be activated separately, and accompanied by a "dark" period where neither is on (to obtain ambient light levels). The sensor records light transmitted or reflected for each LED. The obtained signals can be processed in real time or offline.

The sensors can be utilized in either a transmission or a reflectance mode. In the transmission mode, the sensor is typically attached or clipped to a translucent body part (finger, toe, earlobe, and so forth). The LED light sources that can be located are on one side of a body part, the sensor can be located on the directly opposite side. The light passes through the entirety of the body part, from one side to the other, and is thus modulated by the pulsating arterial blood flow. In the reflectance mode, the light source and the sensor are on the same side of the body part (e.g. forehead, finger, and wrist), and the light is reflected from the skin and the underlying near-surface tissues back to the sensor.

Despite the conceptually different optical paths in the reflectance oximetry, conventional transmission type signal processing for the extraction of oxygen saturation is currently employed; though the sensor part is sometimes adapted to enhance the reflectance signal, the usage of a transmission model for reflectance analysis often results in unstable and erroneous $SpO_2$ estimates.

Wearable monitoring of chronic outpatients can be greatly enhanced by accurate $SpO_2$ measurements, whereas from the usability standpoint a reflectance device which can be attached to body sites such as a wrist or an ankle would impose minimal burden on normal activities; hence, developing reliable reflectance oximetry devices, based on a specific light reflectance model, holds great promise for outpatients suffering from chronic diseases.

SUMMARY

This summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

According to one aspect of the present disclosure, a system for performing pulse oximetry is provided. An example system can include at least one light source operable to emit a light signal for a period of time. The system can include at least one optical sensor operable to detect a modulated light signal. The modulated light signal can include a red signal and an infrared signal. The modulated signal can be a result of an interaction of the light signal with a human tissue. The human tissue can include a pulsatile tissue and a non-pulsatile tissue. The system can further include at least one processor communicatively coupled to the optical sensor. The processor can be operable to process the modulated light signal to estimate at least oxygen saturation in the pulsatile tissue during the time period. The processing can include at least removing a non-pulsatile component due to the interaction of the light signal with the non-pulsatile tissue.

In some embodiments, the pulsatile tissue includes an artery. In certain embodiments the non-pulsatile tissue includes skin. In various embodiments, the human tissue can be associated with a fingertip, a wrist, an ankle, a neck, a chest, and an earlobe.

In some embodiments, the interaction of the light signal with the human tissue can include reflection of the light signal from the human tissue. In other embodiments, the interaction of the light signal with the human tissue can include absorption of the light signal by the human tissue.

In some embodiments, removing the non-pulsatile component includes removing a first parameter from maximums and minimums of intensity associated with the infrared signal and removing a second parameter from maximums and minimums of the intensity associated with the red signal. The first parameter and the second parameter can be pre-determined using a calibration process to reproduce a true value for a ratio $$R = \log\left(\frac{I_H^{ir}}{I_L^{ir}}\right) \bigg/ \log\left(\frac{I_H^{red}}{I_L^{red}}\right),$$

wherein $I_H^{ir}$ is a maximum of intensity of infrared signal, $I_L^{ir}$ is minimum of intensity of the infrared signal, $I_H^{red}$ is a maximum of intensity of the red signal $I_L^{red}$ is a minimum of intensity of the red signal.

In other embodiments, the removing the non-pulsatile component includes multiplying a ratio $$R = \frac{I_H^{ir} - I_L^{ir}}{I_H^{red} - I_L^{red}}$$

by a correction factor, wherein $I_H^{ir}$ is a maximum of intensity of infrared signal, $I_L^{ir}$ is a minimum of intensity of the infrared signal, $I_H^{red}$ is a maximum of intensity of the red signal, $I_L^{red}$ is a minimum of intensity of the red signal. The correction factor can be determined via a calibration process.

According to another aspect of the present disclosure, a method for performing pulse oximetry is provided. An example method includes emitting a light signal for a period of time. The method allows detecting a modulated light signal. The modulated light signal can include a red signal and an infrared signal. The detected signal is a result of an interaction of the light signal with a human tissue. The human tissue includes a pulsatile tissue and a non-pulsatile tissue. The method includes processing the modulated light signal to estimate at least oxygen saturation in the pulsatile tissue during the time period. The processing includes at least removing a non-pulsatile component due to the interaction of the light signal with the non-pulsatile tissue.

According to another example embodiment of the present disclosure, the steps of the method for performing pulse oximetry are stored on a non-transitory machine-readable medium comprising instructions, which when implemented by one or more processors perform the recited steps.

Other example embodiments of the disclosure and aspects will become apparent from the following description taken in conjunction with the following drawings.

BRIEF DESCRIPTION OF THE DRAWINGS

Embodiments are illustrated by way of example and not limitation in the figures of the accompanying drawings, in which like references indicate similar elements.

DETAILED DESCRIPTION

The following detailed description includes references to the accompanying drawings, which form a part of the detailed description. The drawings show illustrations in accordance with exemplary embodiments. These exemplary embodiments, which are also referred to herein as "examples," are described in enough detail to enable those skilled in the art to practice the present subject matter. The embodiments can be combined, other embodiments can be utilized, or structural, logical and electrical changes can be made without departing from the scope of what is claimed. The following detailed description is, therefore, not to be taken in a limiting sense, and the scope is defined by the appended claims and their equivalents.

The present disclosure provides systems and methods for performing pulse oximetry. Embodiments of the present disclosure can allow measuring medical parameters, for example, a photoplethysmogram (PPG) of a patient in a non-intrusive manner while, for example, the patient is at home, at work, outdoors, traveling, or is located at some other stationary or mobile environment. Some embodiments of the present disclosure include a wearable device. The wearable device can be worn at a wrist, ankle, chest, neck, and positioned at other sites of a human body. The wearable device can allow measuring the PPG of the patient without requiring the patient to take an active role in the process. The PPG data collected by the pulse oximetry during an extended period of time can be analyzed to detect and track trends in medical parameters, for example, oxygen saturation, and to make conclusions concerning symptoms and a progression of one or more chronic diseases from which the patient might suffer.

According to some example embodiments, a method for performing pulse oximetry includes emitting a light signal for a period of time. The method allows detecting a modulated light signal. The modulated light signal can include a red signal and an infrared signal. The detected signal is a result of an interaction of the light signal with a human tissue. The human tissue can include a pulsatile tissue and a non-pulsatile tissue. The method includes processing the modulated light signal to estimate at least oxygen saturation in the pulsatile tissue during the time period. The processing includes at least removing a non-pulsatile component due to the interaction of the light signal with the non-pulsatile tissue.

Figure 1:
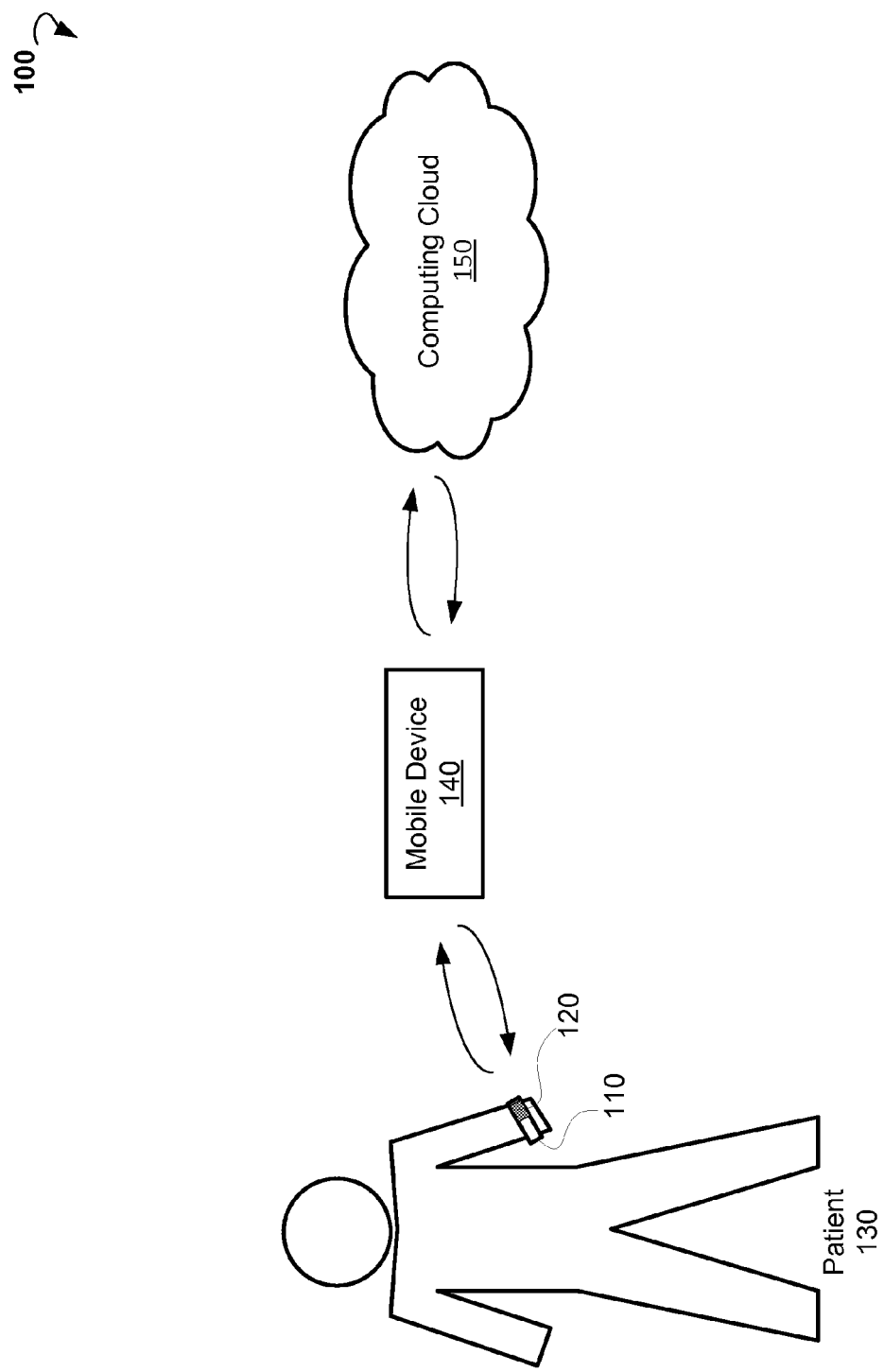
FIG. 1 is a block diagram showing an example system for performing pulse oximetry using a wearable device.

Referring now to FIG. 1, an example system 100 for performing pulse oximetry is shown. The system 100 can include at least a wearable device 110. The wearable device 110 can include sensors 120. In some embodiments, the wearable device 110 is worn by a patient 130 (for example, on a wrist, ankle, earlobe, neck, chest, fingertip, and the like) for an extended period of time. In various embodiments, the wearable device 110 can be carried out as a watch, a bracelet, a wristband, a belt, a neck band, and the like.

The wearable device 110 can be operable to constantly collect, via sensors 120, sensor data from a patient 130. Based on the sensor data, the wearable device 110 can be operable to generate PPG data, and, based on the PPG data, obtain further medical parameters, for example, oxygen saturation, pulse rate, and so forth.

In some embodiments, the system 100 includes a mobile device 140. The mobile device 140 can be communicatively coupled to the wearable device 110. In various embodiments, the mobile device 140 is operable to communicate with the wearable device 110 via a wireless connection such as, for example, Wi-Fi, Bluetooth, Infrared (IR), and the like. The mobile device 140 can include a mobile phone, a smart phone, a phablet, a tablet computer, a notebook, and so forth. The mobile device 140 can be operable to receive the sensors data and analyze the sensor data to generate PPG data.

In further embodiments, the system 100 may include a cloud-based computing resource 150 (also referred to as a computing cloud). In some embodiments, the cloud-based computing resource 150 includes one or more server farms/clusters comprising a collection of computer servers and is co-located with network switches and/or routers. In certain embodiments, the mobile device 140 is communicatively coupled to the computing cloud 150. The mobile device 140 can be operable to send the sensor data to the computing cloud 150 for further analysis (for example, for extracting medical parameters from the sensor data and storing the results). The computing cloud 150 can be operable to run one or more applications and to provide reports regarding health status of the patient, based on trends in medical parameters over time.

Figure 2:
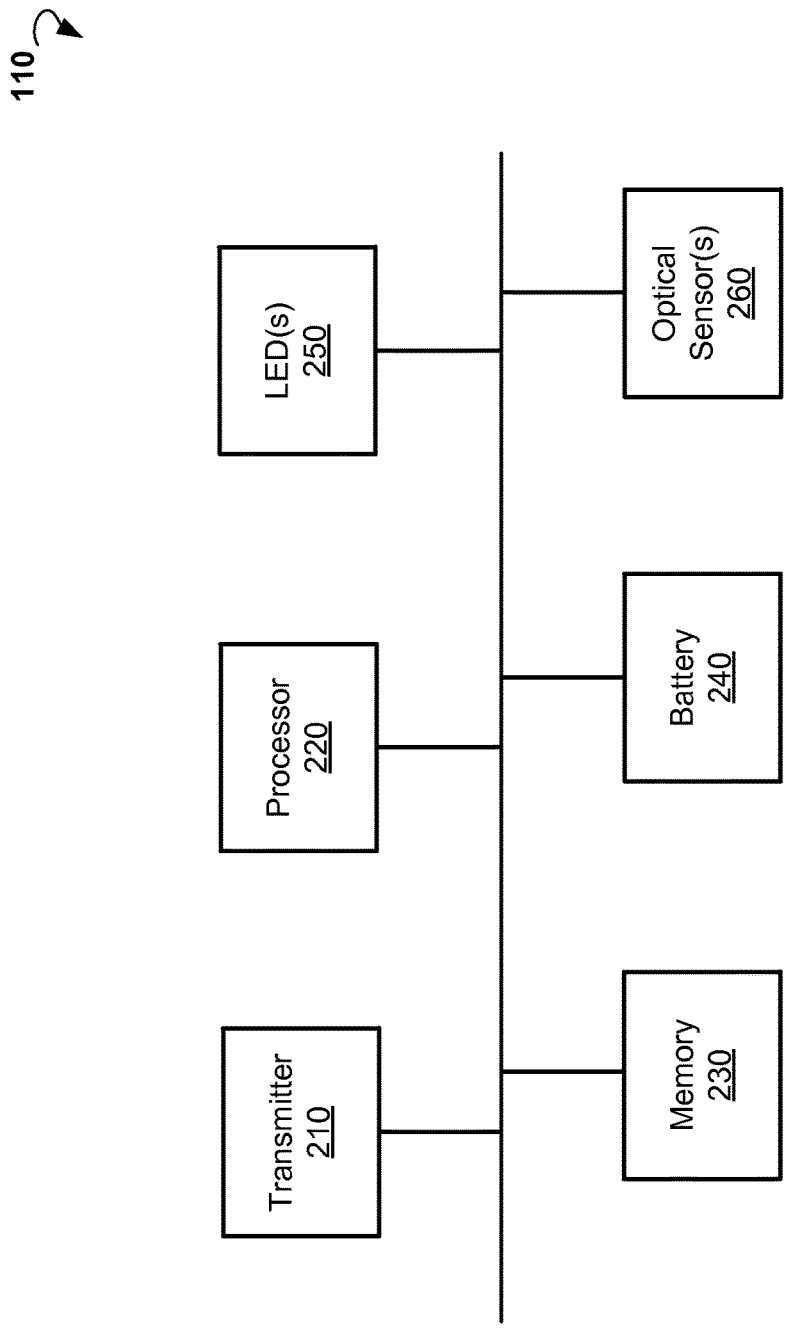
FIG. 2 is a block diagram showing components of an example device for performing pulse oximetry.

FIG. 2 is a block diagram illustrating components of wearable device 110, according to an example embodiment. The example wearable device 110 includes a transmitter 210, a processor 220, memory storage 230, a battery 240, at least two light-emitting diodes 250, and one or more optical sensors 260. The wearable device 110 may comprise additional or different components to provide a particular operation or functionality. Similarly, in other embodiments, the wearable device 110 includes fewer components that perform similar or equivalent functions to those depicted in FIG. 2.

The transmitter 210 can be configured to communicate with a network such as the Internet, a Wide Area Network (WAN), a Local Area Network (LAN), a cellular network, and so forth, to send data streams (for example sensor data, PPG data, and messages).

The processor 220 can include hardware and/or software, which is operable to execute computer programs stored in memory 230. The processor 220 can use floating point operations, complex operations, and other operations, including processing and analyzing sensor data.

In some embodiments, the battery 240 is operable to provide electrical power for operation of other components of the wearable device 110. In some embodiments, the battery 240 is a rechargeable battery. In certain embodiments, the battery 240 is recharged using an inductive charging technology.

In various embodiments, the LEDs 250 are operable to emit light signals of a red wavelength (typically 660 nm) and infrared wavelength (660 nm). Each of the LEDs is activated separately and accompanied by a "dark" period where neither of the LEDs is on to obtain ambient light levels. In some embodiments, a single LED can be used to emit the both infrared and red light signals. The lights can be absorbed by human blood (mostly by hemoglobin). The methods for pulse oximetry are based on the fact that oxygenated hemoglobin absorbs more infrared light while deoxygenated hemoglobin absorbs more red light. Oxygenated hemoglobin allows more red light to pass through while deoxygenated hemoglobin allows more infrared light to pass through. The optical sensor(s) 260 (typically a photodiode) can receive light signals modulated by a human tissue. Based on the changes in the intensities of the modulated light signals, one or more medical parameters, such as, for example, oxygen saturation, arterial blood flow, pulse rate, and respiration can be determined.

The LEDs 250 and optical sensor(s) 260 can be utilized in either a transmission or a reflectance mode for pulse oximetry. In the transmission mode, the LEDs 250 and sensor 260 are typically attached or clipped to a translucent body part (e.g., a finger, toe, and earlobe). The LEDs 250 are located on one side of the body part while the optical sensor(s) 260 are located directly on the opposite site. The light passes through the entirety of the body part, from one side to the other, and is thus modulated by the pulsating arterial blood flow. In the reflectance mode, the LEDs 250 and optical sensor(s) 260 are located on the same side of the body part (e.g. a forehead, finger, and wrist), and the light is reflected from the skin and underlying near-surface tissues back to the optical sensor(s) 260.

Figure 3B:
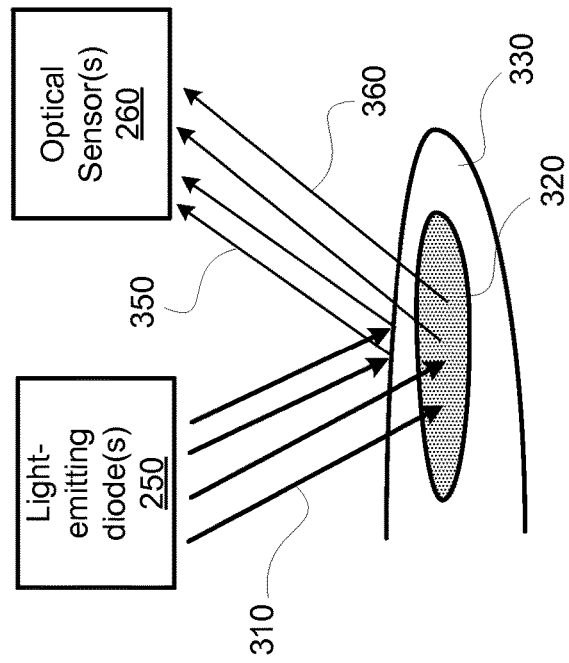
FIG. 3B is a block diagram illustrating example details of reflectance pulse oximetry.
Figure 3A:
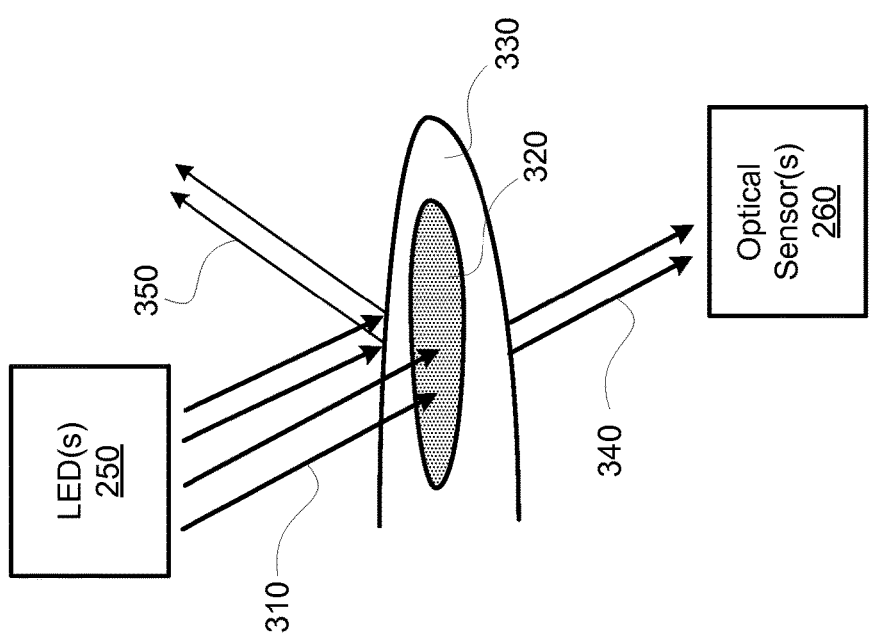
FIG. 3A is a block diagram illustrating example details of transmission pulse oximetry.

FIG. 3A is a block diagram illustrating details of transmission pulse oximetry. The light signals 310 emitted by LEDs 250 in red and infrared wavelengths are transmitted through highly perfused pulsatile tissue 320 (for example, blood vessels in a fingertip or an earlobe). The light signals 340 modulated across the pulsatile tissue 320 can be detected by optical sensor(s) 260. Some portions of the light signals 310 are reflected by non-pulsatile tissue 330 to produce a reflected light signal 350. The detected light signal 340, I can be evaluated as follows:

$$I = I_0 K e^{-cd}$$

where $I_0$ is a LED intensity, K is a characteristic transmission coefficient of non-pulsating tissue, d is an effective diameter of pulsating blood vessels 320, and c is a light attenuation coefficient of blood fluid.

In the traditional approach, the transmission pulse oximetry assumes that all detected light passes through pulsating blood vessels and the $e^{-cd}$ term expresses the attenuation of light by the blood fluid (mostly by hemoglobin) according to the Beer-Lambert law.

The diameter of the blood vessel 320 has periodic variation according to pulse rate frequency with maximum and minimum values:

$$I_H = I_0 K e^{-cd_{min}}; \quad I_L = I_0 K e^{-cd_{max}}$$

A ratio between the minimum and maximum values is:

$$\frac{I_h}{I_L} = \frac{I_0 K e^{-cd_{min}}}{I_0 K e^{-cd_{max}}} = e^{c(d_{max} - d_{min})}$$

A ratio R can be defined as the ratio between the logarithmic values of ratios as follows:

$$R = \frac{\log\left(\frac{I_H^{red}}{I_L^{red}}\right)}{\log\left(\frac{I_H^{ir}}{I_L^{ir}}\right)} = \frac{\log(I_H^{red}) - \log(I_L^{red})}{\log(I_H^{ir}) - \log(I_L^{ir})} = \frac{c^{red}(d_{max} - d_{min})}{c^{ir}(d_{max} - d_{min})} = \frac{c^{red}}{c^{ir}}$$

The ratio R expresses the ratio between the attenuation coefficients at the transmission frequencies of red and infrared wavelengths. The ratio R can indicate a ratio between oxygenated hemoglobin and deoxygenated hemoglobin. The ratio R can be converted to a corresponding oxygen saturation (SpO$_2$) value via an empirically-derived look-up table.

FIG. 3B is a block diagram illustrating details of reflectance pulse oximetry. Unlike the transmission pulse oximetry, light signals 310 emitted by LEDs 250 is reflected back to the optical sensor(s) 260 from both pulsatile tissue 320 (pulsating arteries) and non-pulsatile tissue 330 (e.g., skin and underlying tissue). In FIG. 3B, the corresponding reflected light signals are denoted as signal 360 and signal 350. The reflected signal 350 from non-pulsatile tissue 330 has a negligible significance in conventional transmission oximetry (see FIG. 3A), as well as in strong signal reflectance oximetry when, for example, operated on a highly perfused tissue such as a fingertip or a forehead.

In case of a weak pulsatile signal, the non-pulsatile tissue reflection should be accounted for in order to avoid an erroneous SpO$_2$ reading. Therefore, the contribution of the non-pulsatile tissue needs to be identified and accounted for, to enable an accurate SpO$_2$ reading in such cases.

Figure 4:
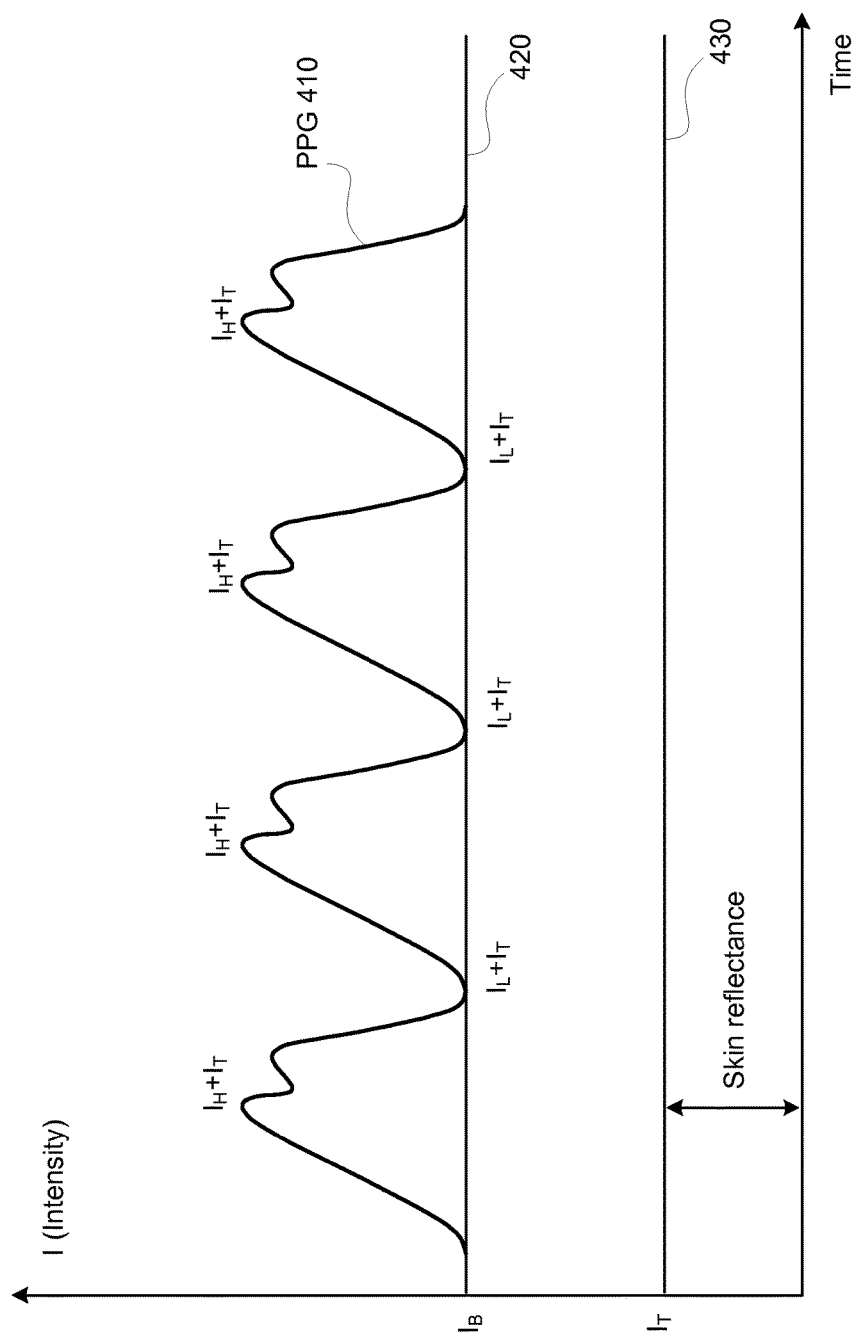
FIG. 4 shows an example plot of a photoplethysmogram (PPG).

FIG. 4 shows a plot of example PPG 410 which can be obtained with reflectance pulse oximetry. The PPG represents the intensity I of the light signal 310 (either the red signal or the infrared signal) as modulated by a human tissue mostly due to a blood flow. Both the high peaks $I_H$ and low peaks $I_L$ of the PPG 410 include a component $I_T$ due to the non-pulsatile tissue reflection. The line 420 illustrates a base intensity line for PPG and the line 430 illustrates the addition in intensity of reflected signal I due to non-pulsatile tissue (for example, skin). The following embodiments can be used to estimate the additive contribution of the non-pulsatile tissue.

Embodiment 1

According to an example embodiment of present technology, the detected signal I can be modeled as follows:

$$I = I_0(K_1 + K_2 e^{-cd})$$

While in the transmission oximetry $K_1$ is small relative to $K_2$ and may be thus neglected in both red and infrared measurements, it may not be neglected in weak signal cases such as in the general reflectance oximetry or in the low perfusion transmission oximetry.

Let us consider the following modification. Let $L^{red}>0$, $L^{ir}>0$ denote arbitrary scalars, representing the bias generated by the non-pulsatile signal components:

$$R_1(L^{red}, L^{ir}) = \frac{\log\left(\frac{I_H^{red} - L^{red}}{I_L^{red} - L^{red}}\right)}{\log\left(\frac{I_H^{ir} - L^{ir}}{I_L^{ir} - L^{ir}}\right)}$$

It can be shown that $R_1(I_0 K_1^{red}, I_0 K_1^{ir}) = R$. The desired constants $L^{red} = I_0 K_1^{red}$ and $L^{ir} = I_0 K_1^{ir}$ can be found during a calibration process, where a gold standard measurement provides the true R value $R = R_{true}$ and the resulting constants $(L^{red}, L^{ir})$ are optimized to fulfill the equation $R_1(L^{red}, L^{ir}) = R_{true}$.

Embodiment 2

According to another embodiment of present technology, the alternating current (AC) component of the PPG signal I (i.e. the difference between maximum and minimum values), assuming a small change in blood vessel size, may be expressed as $$AC = I_H - I_L = I_0 K_2 (e^{-cd_{min}} - e^{-cd_{max}}) = I_0 K_2 e^{-cd_{max}} (e^{-c(d_{max} - d_{min})} - 1)$$

$$\approx I_0 K_2 e^{-cd_{max}} c(d_{min} - d_{max})$$

and therefore $$\frac{AC^{red}}{AC^{ir}} \approx \frac{I_0^{red} K_2^{red} e^{-c^{red} d_{max}} * c^{red}(d_{min} - d_{max})}{I_0^{ir} K_2^{ir} e^{-c^{ir} d_{max}} * c^{ir}(d_{min} - d_{max})} =$$

$$\frac{I_0^{red} K_2^{red}}{I_0^{ir} K_2^{ir}} e^{-(c^{ir} - c^{red})d_{max}} * R$$

Denoting $$R_2(M) = \frac{1}{M} \frac{AC^{red}}{AC^{ir}}$$

results in $$R_2\left(\frac{I_0^{red} K_2^{red}}{I_0^{ir} K_2^{ir}}\right) = R_{true}.$$

The correction factor M can be estimated during a calibration process and can be used in subsequent measurements to calibrate the measured R value.

In certain instances, calibration of the device 110 might be requested by the device itself when the calculated SpO2 value is not as expected, for example if it is outside a predefined range. The device 110 might also signal that calibration is needed if calculated values vary substantially from normal values recorded for a given user, patient, etc. In such as case, the device 110 might proactively request re-calibration. If readings remain outside the expected range, a warning (audible, tactile, visual or the like) may be generation. If recalibration of the device 110 causes the measured values to return to the expected range, then the new calibration parameters are maintained and normal operation resumes.

In various embodiments, Higher Order Statistic, Principal Component Analysis, and other methods can be used to optimize the calibration process.

The PPG signal 410 (FIG. 4) can be contaminated by a noise due to environment conditions, activity of a user of the wearable device 110 and behavior of the user. For example, movements of the user can affect the detection by optical sensor(s) 260 of the reflected or absorbed light signal(s). Temperature changes can affect blood flow to the area with the sensor. Sweating of user can also affect the optical quality of the optical sensor(s) 260.

In various embodiments, to remove the noise in PPG signal, a band-pass filter can be applied to a raw PPG signal to remove all frequencies outside the range of a heart beat rate typical for a human. For example, the band-pass filter can remove all frequencies outside the range from 30 to 300 per minute.

Additionally, in some embodiments, the noise and waveforms in PPG signal can be separated using an autoregressive (AR) model. The PPG waveform can be modeled with a low order AR model. The AR model can identify the pulse frequency in the PPG signal even for short time signal segments. After identifying the pulse rate frequency, AR band-pass filter can be constructed. The AR band-pass filter can allow passing frequencies within a certain range around the pulse rate frequency (for example +/−10% from the pulse rate frequency) to filter out all frequencies outside the range. As a result, a clean PPG signal can be generated. The clean PPG signal can be used to determine a ratio for SpO₂ oxygen saturation according to embodiments of present disclosure.

Figure 5:
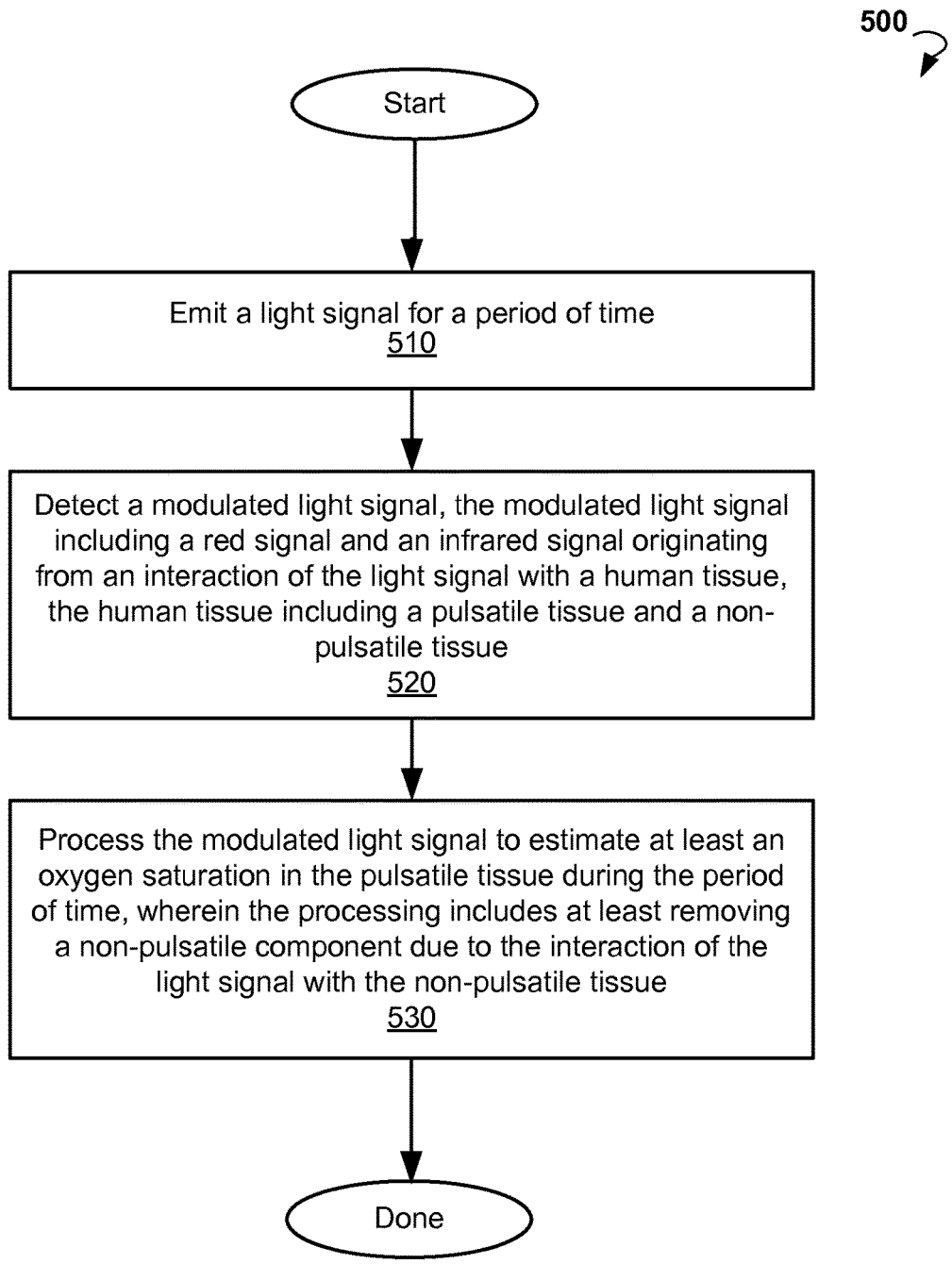
FIG. 5 is a flow chart showing an example method for performing pulse oximetry.

FIG. 5 is a flow chart of a method 500 for data collected from a single wrist, according to an example embodiment. Method 500 can commence at block 510 with emitting a light signal for a period of time. At block 520, the method 500 can proceed with detecting a modulated light signal. The modulated light signal can include a red signal and an infrared signal. The detected signal can be a result of interaction of the light signal with a human tissue. The human tissue can include a pulsatile tissue and a non-pulsatile tissue.

At block 530, the method 500 can process the modulated light signal to estimate at least oxygen saturation in the pulsatile tissue during the time period. The processing can include at least removing a non-pulsatile component due to the interaction of the light signal with the non-pulsatile tissue. In some embodiments, the non-pulsatile component is removed by removing a first parameter from maximums and minimums of an intensity associated with the infrared signal and removing a second parameter from maximums and minimums of the intensity associated with the red signal. The first parameter and the second parameter can be pre-determined using a calibration process to reproduce a true value for $$\text{ratio} = \log\left(\frac{I_H^{ir}}{I_L^{ir}}\right) / \log\left(\frac{I_H^{red}}{I_H^{red}}\right),$$

wherein $I_H^{ir}$ is a maximum of intensity of infrared signal, $I_L^{ir}$ is a minimum of intensity of the infrared signal, $I_H^{red}$ is a maximum of intensity of the red signal, and $I_L^{red}$ is a minimum of intensity of the red signal.

In other embodiments, the non-pulsatile component is removed by multiplying a ratio $$R = \frac{I_H^{ir} - I_L^{ir}}{I_H^{red} - I_L^{red}}$$

by a correction factor, wherein $I_H^{ir}$ is a maximum of intensity of infrared signal, $I_L^{ir}$ is a minimum of intensity of the infrared signal, $I_H^{red}$ is a maximum of intensity of the red signal $I_L^{red}$ is a minimum of intensity of the red signal. The correction factor can be pre-determined via a calibration process.

Examples

Figure 6:
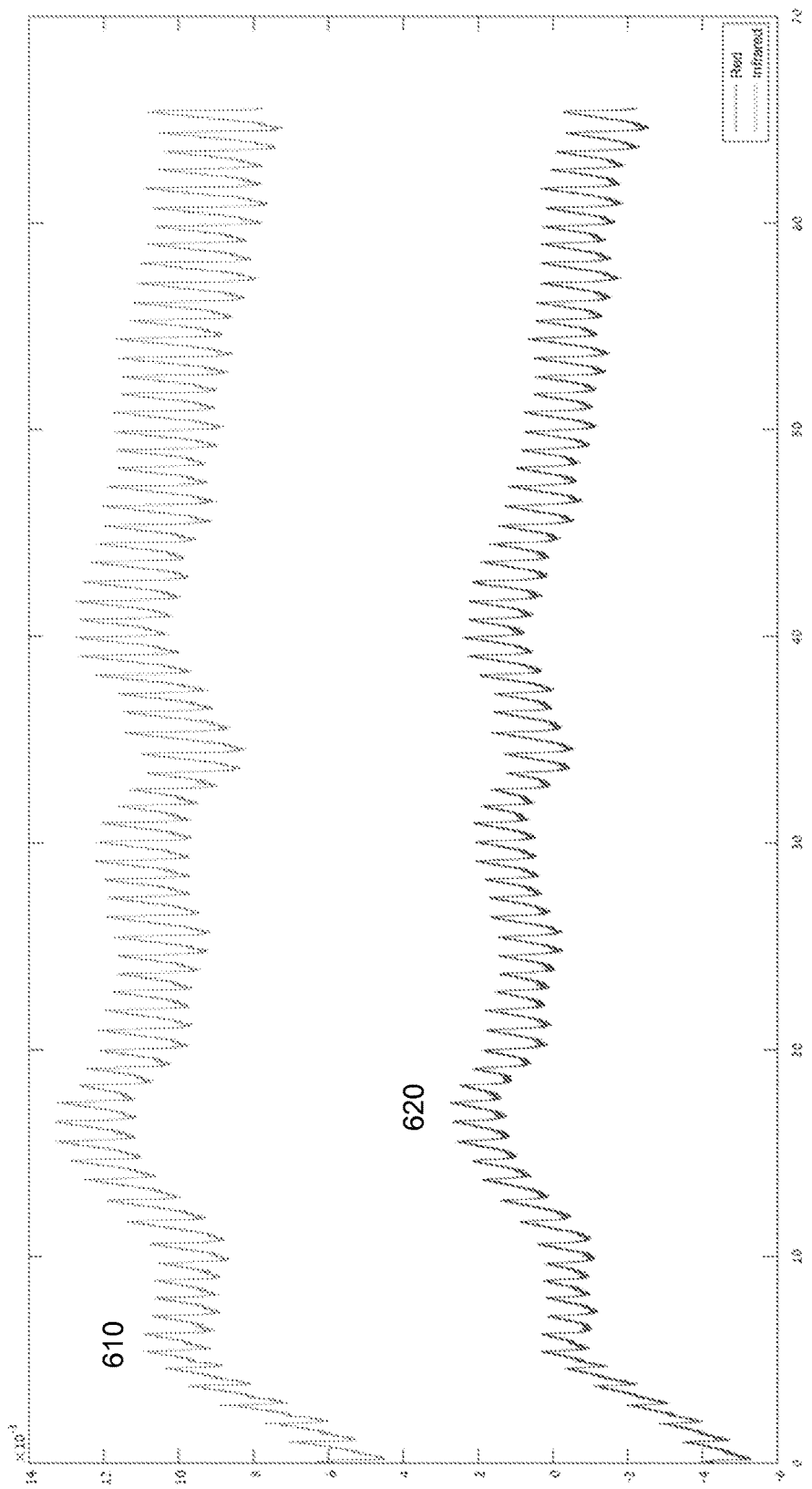
FIG. 6 illustrates example plots of a raw infrared PPG signal and a raw red PPG signal.

FIG. 6 illustrates example plots of a raw infrared signal 610 and raw red signal 620 measured during a period of 1 minute. The red signal 620 can be shifted.

Figure 7:
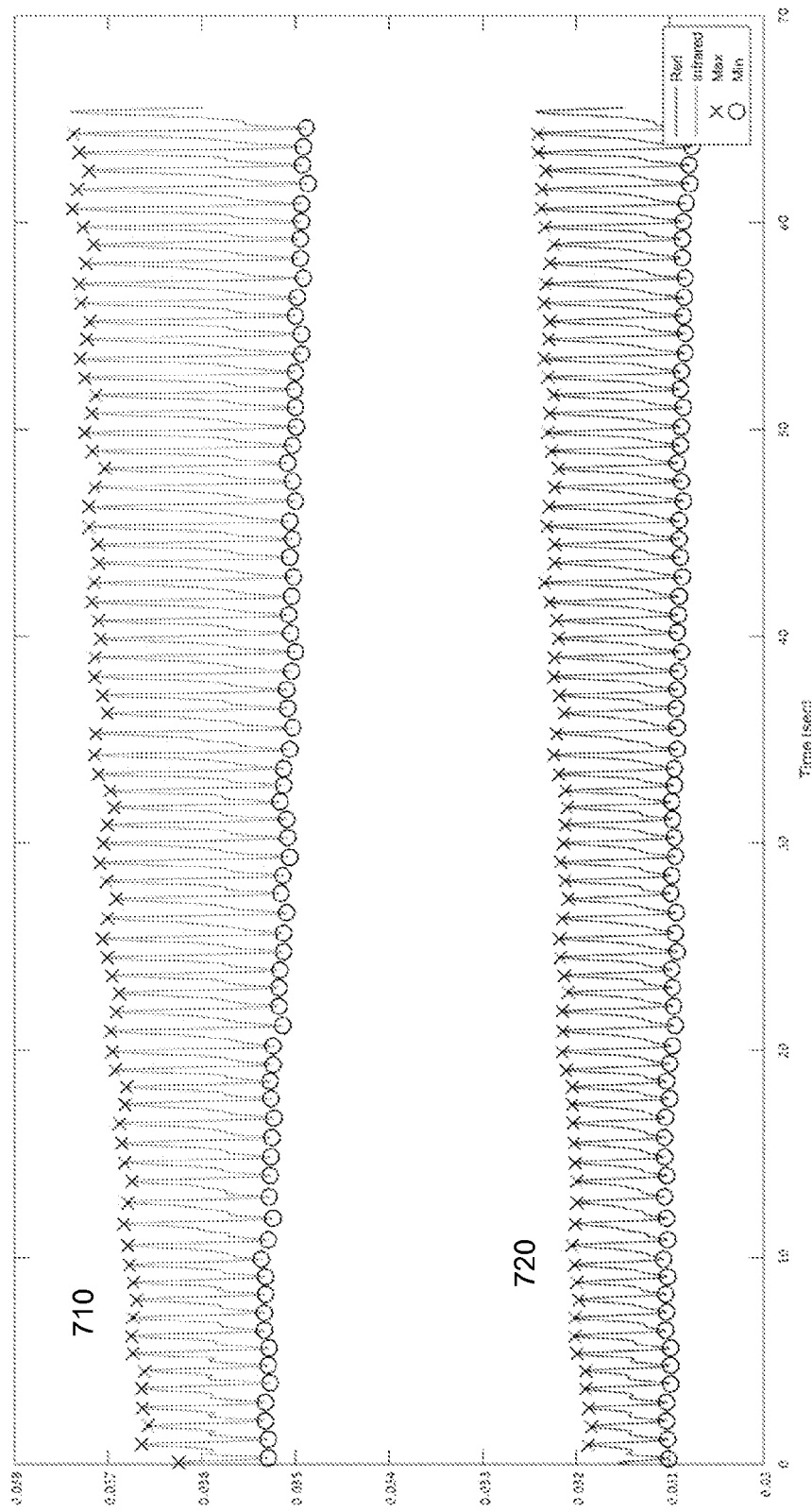
FIG. 7 illustrates example plots of a band-pass filtered infrared PPG signal and a band-passed filtered red PPG signal.

FIG. 7 illustrates example plots of infrared signal 710 and red signal 720. The infrared signal 710 can be obtained from the raw infrared signal 610 by band-pass filtering. The red signal 720 is band-passed filtered raw red signal 620.

Figure 8:
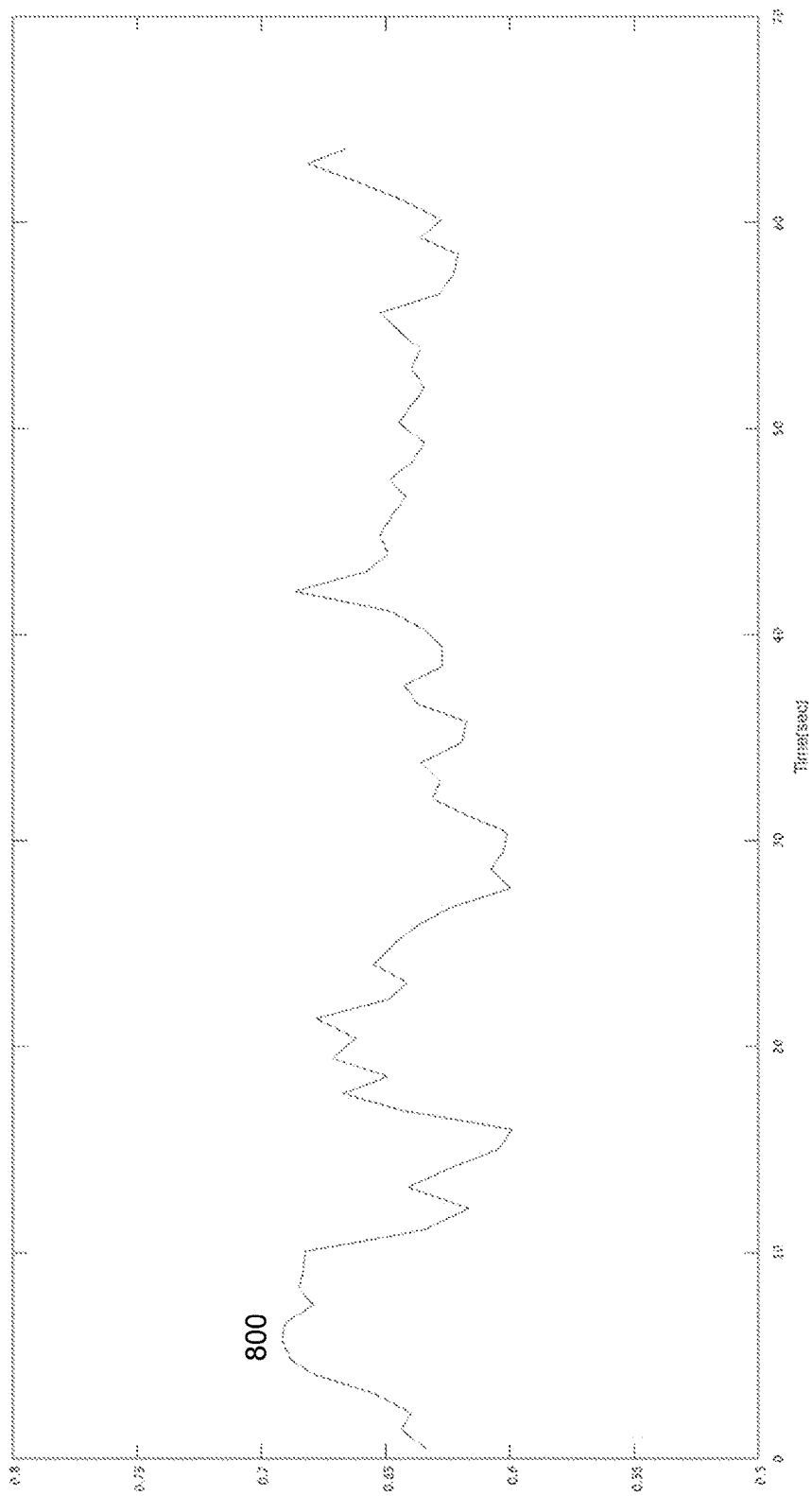
FIG. 8 illustrates an example plot of a ratio for determining the SpO$_2$ oxygen saturation.
Figure 9:
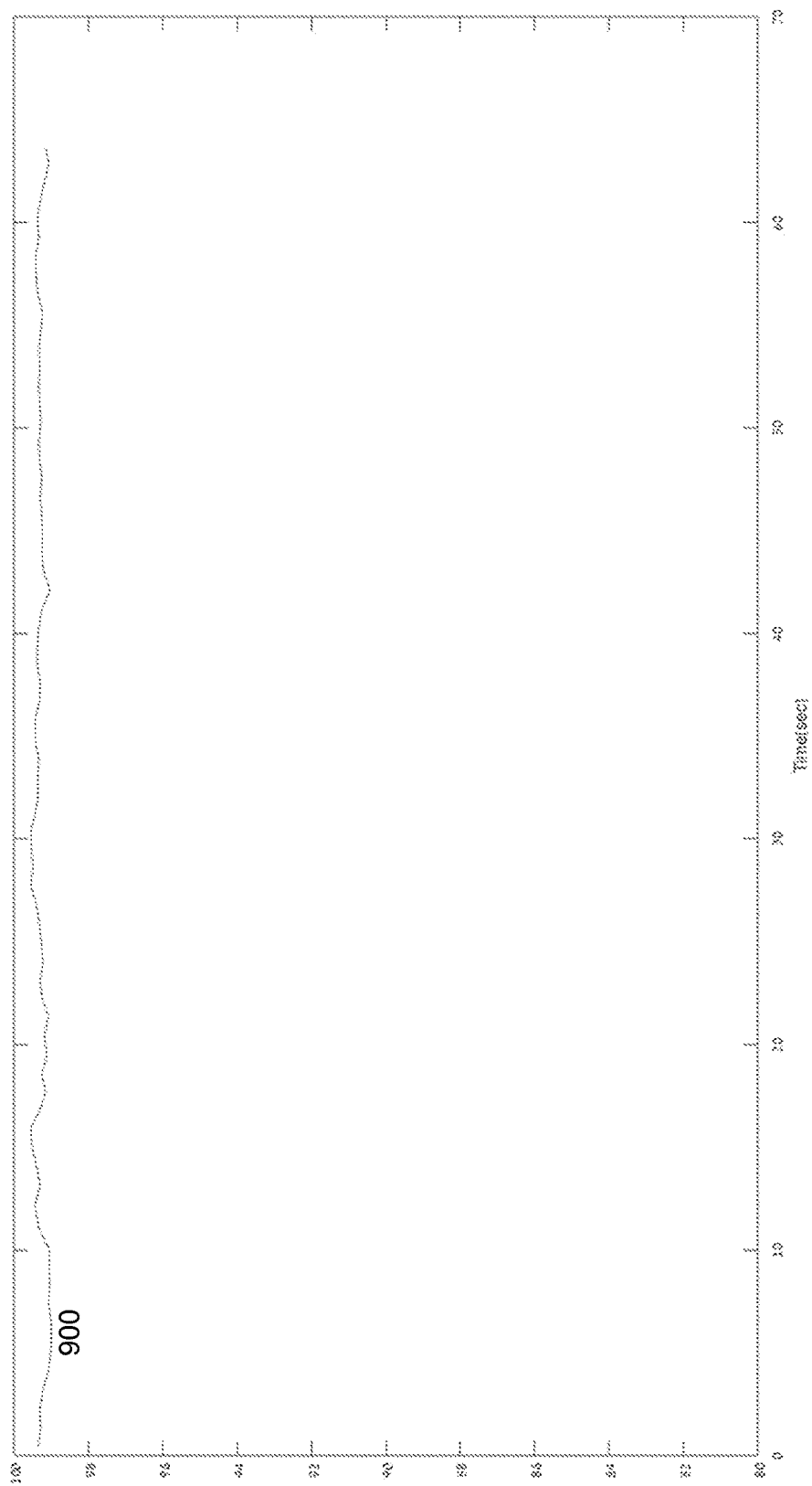
FIG. 9 illustrates an example plot of SpO$_2$ oxygen saturation determined based on the ratio of FIG. 8.
Figure 10:
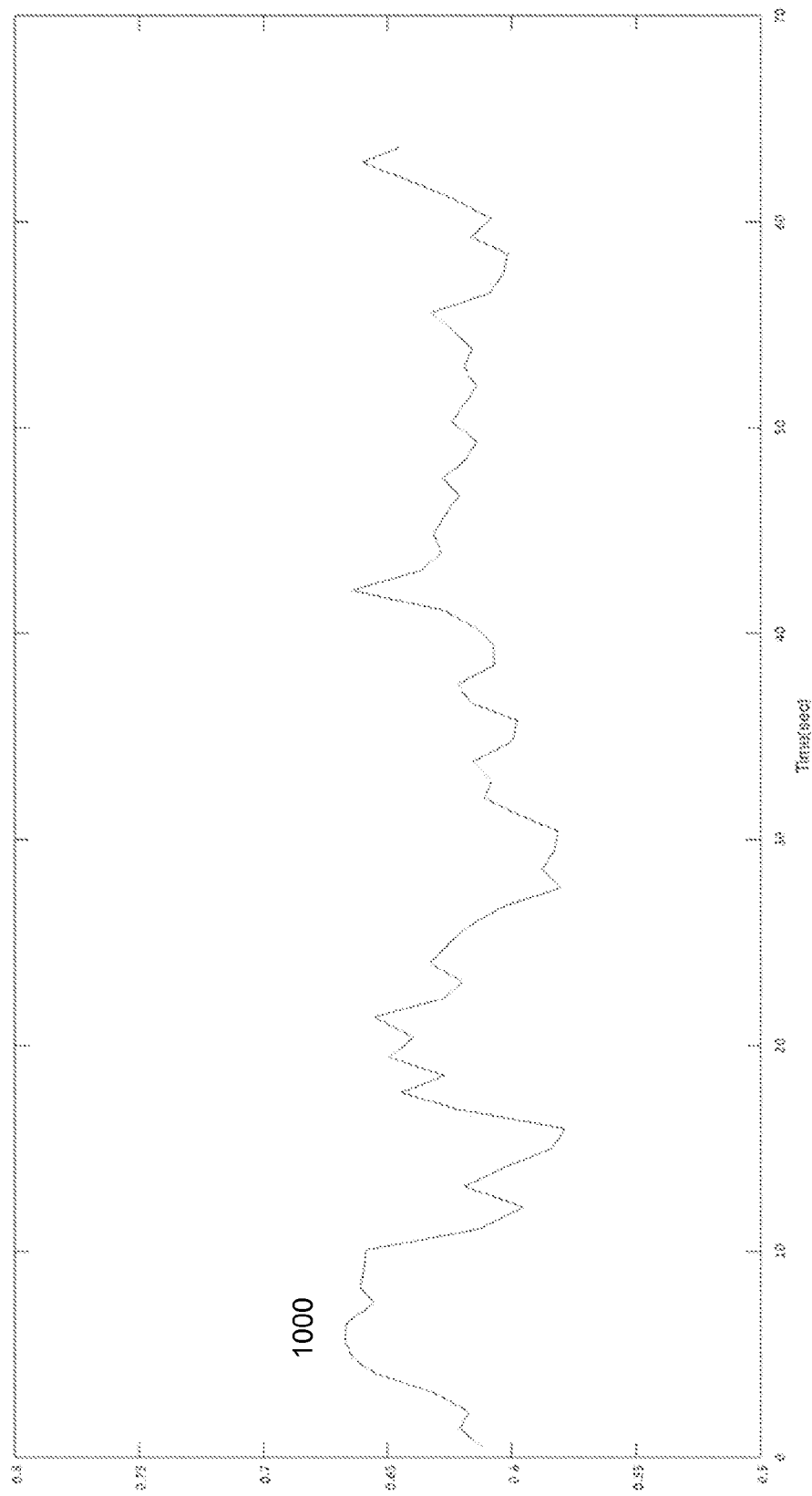
FIG. 10 illustrates example plot of a ratio for determining the SpO$_2$ oxygen saturation.
Figure 11:
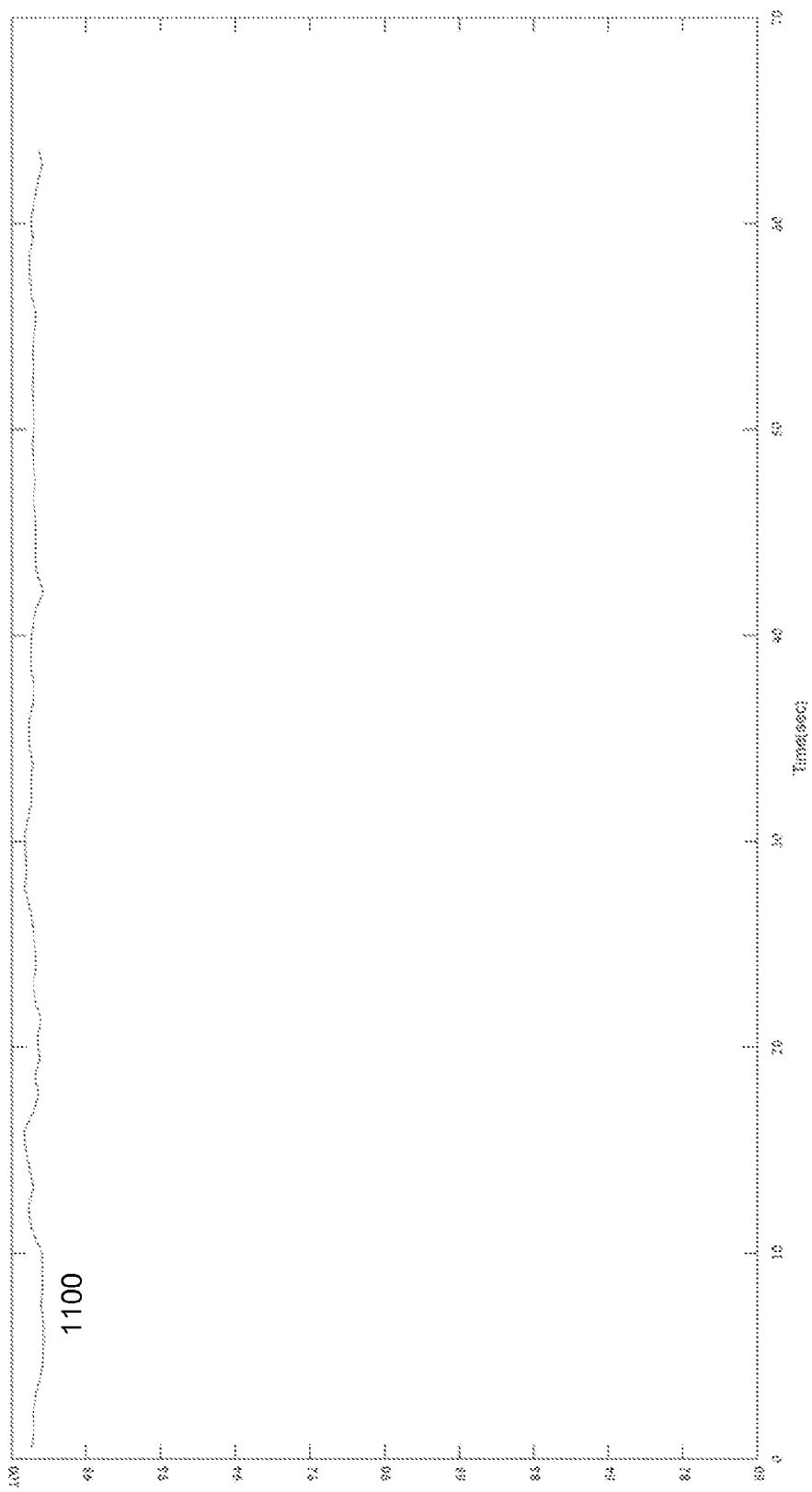
FIG. 11 illustrates an example plot of SpO$_2$ oxygen saturation determined based on the ratio of FIG. 10.

FIG. 8 illustrated an example plot of a ratio 800 for determining the SpO₂ saturation. The ratio 800 can be determined based on the band-filtered infrared signal 710 and red signal 720 using the method of embodiment No 1 described above. FIG. 9 illustrates an example plot of SpO₂ oxygen saturation determined based on ratio 900. FIG. 10 illustrates an example plot of ratio 1000 for determining SpO₂ oxygen saturation. The ratio 1000 can be determined based on band-pass filtered infrared signal 710 and band-pass filtered red signal 720 using the method of embodiment No 2 described above. FIG. 11 illustrates an example plot of SpO₂ oxygen saturation determined based on ratio 1100.

What is claimed is:

1. A method for performing a pulse oximetry, the method comprising:
    emitting, by at least one light source of a wearable device, a red signal and an infrared signal at a human tissue, the human tissue including a pulsatile tissue and a non-pulsatile tissue;
    detecting, by at least one optical sensor of the wearable device, a first signal, the first signal representing an intensity of a modulated red signal, the modulated red signal being generated by an interaction of the red signal with the human tissue;
    detecting, by the at least one optical sensor of the wearable device, a second signal, the second signal representing an intensity of a modulated infrared signal, the modulated infrared signal being generated by an interaction of the infrared signal with the human tissue;
    shifting, by at least one processor communicatively connected to the at least one optical sensor, the first signal by a first parameter $L^{red}$ to account for a contribution to the first signal due to a reflection of the red signal from the non-pulsatile tissue;
    shifting, by the at least one processor, the second signal by a second parameter $L^{ir}$ to account for a contribution to the second signal due to a reflection of the infrared signal from the non-pulsatile tissue;

determining, by the at least one processor and based on the shifted first signal and the shifted second signal, a ratio for obtaining an oxygen saturation;

determining, by the at least one processor and based on the ratio, a value of the oxygen saturation; wherein $L^{red}$ and $L^{ir}$ are positive arbitrary scalars pre-determined in a calibration process, the calibration process including determination of $L^{red}$ and $L^{ir}$ based on a relationship $\log((I_H^{red}-L^{red})/(I_L^{red}-L^{red}))/\log((I_H^{ir}-L^{ir})/(I_L^{ir}-L^{ir}))=R_{true}$, wherein $R_{true}$ is a true ratio for obtaining the oxygen saturation, $I_H^{red}$ is a maximum of the first signal, $I_L^{red}$ is a minimum of the first signal, $I_L^{ir}$ is a maximum of the second signal, and $I_H^{ir}$ is a minimum of the second signal; and wherein the value of the oxygen saturation is used to provide reports on a symptom or a progression of one or more chronic diseases of a user.

2. The method of claim 1, wherein the pulsatile tissue includes an artery.

3. The method of claim 1, wherein the non-pulsatile tissue includes skin.

4. The method of claim 1, wherein the human tissue includes one of the following: a fingertip, a wrist, an ankle, a neck, a chest, and an earlobe.

5. The method of claim 1, wherein the modulated red signal is obtained as result of reflection of the red signal from the human tissue and the modulated infrared signal is obtained as result of reflection of the infrared signal from the human tissue.

6. The method of claim 1, wherein the modulated red signal is obtained as a result of transmission of the red signal through the human tissue and the modulated infrared signal is obtained as result of transmission of the infrared signal through the human tissue.

7. A system for performing a pulse oximetry, the system comprising:

a wearable device including:

at least one light source configured to emit a red signal and an infrared signal at a human tissue of a user, the human tissue including a pulsatile tissue and a non-pulsatile tissue; and at least one optical sensor configured to:

detect a first signal, the first signal representing an intensity of a modulated red signal, the modulated red signal being a result of an interaction of the red signal with the human tissue; and detect a second signal, the second signal representing an intensity of a modulated infrared signal, the modulated infrared signal being a result of an interaction of the infrared signal with the human tissue; and at least one processor communicatively connected to the at least one optical sensor and configured to:

shift the first signal by a first parameter $L^{red}$ to account for contribution due to reflection of the red signal from the non-pulsatile tissue;

shift the second signal by a second parameter $L^{ir}$ to account for contribution due to reflection of the infrared signal from the non-pulsatile tissue;

determine, based on the shifted first signal and the shifted second signal, a ratio to be used to obtain an oxygen saturation; and determine, based on the ratio, a value of the oxygen saturation; wherein $L^{red}$ and $L^{ir}$ are positive arbitrary scalars pre-determined in a calibration process, the calibration process including determination of $L^{red}$ and $L^{ir}$ based on a relationship $\log((I_H^{red}-L^{red})/(I_L^{red}-L^{red}))/\log((I_H^{ir}-L^{ir})/(I_L^{ir}-L^{ir}))=R_{true}$, wherein $R_{true}$ is a true ratio for obtaining the oxygen saturation, $I_H^{red}$ is a maximum of the first signal, $I_L^{red}$ is a minimum of the first signal, $I_H^{ir}$ is a maximum of the second signal, and $I_L^{ir}$ is a minimum of the second signal; and a cloud-based computing resource configured to provide, based on the value of the oxygen saturation, reports on a symptom or a progression of one or more chronic diseases of the user.

8. The system of claim 7, wherein the at least one processor is further configured to:

determine that the value of the oxygen saturation is outside a predefined range of values; and in response to the determination, prompt performing a re-calibration process to obtain a new first parameter and a new second parameter.

9. The system of claim 8, wherein the predefined range of values is specific for the user.

10. The system of claim 7, wherein the wearable device is configured to be positioned at one of the following: a fingertip, a wrist, an ankle, a neck, a chest, and an earlobe of the user.

11. The system of claim 7, wherein the at least one optical sensor is configured to detect the first signal upon a reflection of the red signal from the human tissue and to detect the second signal upon a reflection of the infrared signal from the human tissue.

12. The system of claim 7, wherein the at least one optical sensor is configured to detect the first signal upon transmission of the red signal through the human tissue and to detect the second signal upon transmission of the infrared signal through the human tissue.

13. The system of claim 7, wherein the at least one light source and the at least one optical sensor are configured to be located on opposite sides of a body part.

14. The system of claim 7, wherein the at least one light source and the at least one optical sensor are configured to be located on a same side of a body part.

15. The system of claim 7, further comprising a transmitter, the transmitter being configured to communicate data over a network.

16. The system of claim 7, further comprising a mobile device communicatively connected to the wearable device.

17. The system of claim 16, wherein the at least one optical sensor is further configured to send data collected by the at least one optical sensor to the mobile device.

18. A non-transitory computer-readable storage medium having embodied thereon instructions, which when executed by a processor, causes a system to perform steps of a method, the method comprising:

emitting at a human tissue, by at least one light source of a wearable device, a red signal and an infrared signal, the human tissue including a pulsatile tissue and a non-pulsatile tissue;

detecting, by at least one optical sensor of the wearable device, a first signal, the first signal representing an intensity of a modulated red signal, the modulated red signal being a result of interaction of the red signal with the human tissue;

detecting, by the at least one optical sensor of the wearable device, a second signal, the second signal representing an intensity of a modulated infrared signal, the modulated infrared signal being a result of interaction of the infrared signal with the human tissue;

shifting the first signal by a first parameter $L^{red}$ to account for a contribution due to reflection of the red signal from the non-pulsatile tissue;

shifting the second signal by a second parameter $L^{ir}$ to account for contribution due to reflection of the infrared signal from the non-pulsatile tissue;

determining, based on the shifted first signal and the shifted second signal, a ratio to be used to obtain an oxygen saturation;

determining, based on the ratio, a value of the oxygen saturation; wherein $L^{red}$ and $L^{ir}$ are positive arbitrary scalars pre-determined in a calibration process, the calibration process including determination of $L^{red}$ and $L^{ir}$ based on a relationship $\log((I_H^{red}-L^{red})/(I_L^{red}-L^{red}))/\log((I_H^{ir}-L^{ir})/I_L^{ir}-L^{ir}))=R_{true}$, wherein $R_{true}$ is a true ratio for obtaining the oxygen saturation, $I_H^{red}$ is a maximum of the first signal, $I_L^{red}$ is a minimum of the first signal, $I_H^{ir}$ is a maximum of the second signal, and $I_L^{ir}$ is a minimum of the second signal; and providing reports on a symptom or a progression of one or more chronic diseases of a user based on the value of the oxygen saturation.

\* \* \* \* \*